United States Patent [19]

Gut et al.

[11] Patent Number: 4,505,934

[45] Date of Patent: Mar. 19, 1985

[54] INSECTICIDE COMPOSITION, ITS PREPARATION AND ITS USE

[75] Inventors: Jiri Gut, Delft; Adriaan M. van Oosten, Maassluis, both of Netherlands

[73] Assignee: Nederlandse Centrale Organisatie Voor Toegepast-Natuurwetenschappelijk Onderzoek, The Hague, Netherlands

[21] Appl. No.: 407,042

[22] Filed: Aug. 11, 1982

[30] Foreign Application Priority Data

Aug. 21, 1981 [NL] Netherlands ............... 8103905

[51] Int. Cl.$^3$ ............................................. A01N 27/00
[52] U.S. Cl. ..................................................... 514/762
[58] Field of Search ........................................ 424/355

[56] References Cited

U.S. PATENT DOCUMENTS 3,665,040  5/1972  Ruegg et al. ................ 424/325

OTHER PUBLICATIONS

C.A., 89: 124503y, (Hille Ris Lambers et al.).
C.A., 88: 147466g, (Montgomery et al.).
Science, "Aphid Alarm Pheromone: Isolation, Identification, Synthesis", vol. 177, Sep., 1972, pp. 1121–1122.
Nature, "Trans—$\beta$—farnesene, Alarm Pheromone of the Green Peach Aphid, Myzus persicae (Sulzer)", vol. 241, Jan. 12, 1973, pp. 126–127.
Experientia, "Alarm Pheromone of Grain Aphids", vol. 29, 1973, pp. 658–660.
D. C. Griffiths et al.: "A Potential Application of Aphid Alarm Pheromones", Entomologia Experimentalis Et Applicata, vol. 27, No. 2, 1980, pp. 199–201.

Primary Examiner—Albert T. Meyers
Assistant Examiner—F. Abramson
Attorney, Agent, or Firm—Brumbaugh, Graves, Donohue & Raymond

[57] ABSTRACT

Insecticide composition comprising (E)-$\beta$-farnesene as a contact insecticide against aphids, a process for preparing said composition and the use of the (E)-$\beta$-farnesene for controlling aphids.

4 Claims, No Drawings

INSECTICIDE COMPOSITION, ITS PREPARATION AND ITS USE

The invention relates to the control of aphids (Aphididae).

It was found that (E)-β-farnesene, that is to say the trans form of 7,11-dimethyl-3-methylene-1,6,10-dodecatriene, has a killing effect on aphids when the aphids are contacted with this compound in liquid form. This finding is surprising, since it is known that aphids secrete this substance which has as the activity of an alarm pheromone [Science 177, 1121 (1972), Nature 241, 126 (1973) and Experientia 29, 658–660 (1973)] and in view of the fact that, generally, aphids have good resistance against direct contact with solvent droplets, such as of absolute ethanol and acetone.

Consequently, the invention relates to a composition which is active as a contact insecticide against aphids, comprising an amount of (E)-β-farnesene. Further, the invention relates to a process for preparing a composition which is active as a contact insecticide against aphids, according to which process (E)-β-farnesene is mixed with one or more solvents and/or diluents and, optionally, surfactants.

Further, the invention relates to the use of (E)-β-farnesene in liquid form as a contact insecticide against aphids, or, in other words, to a process for controlling aphids in which the aphids are contacted with (E)-β-farnesene in liquid form.

The (E)-β-farnesene has to be used in liquid form. In the form of the vapour the substance acts as an alarm pheromone only. The expression "liquid form" means (E)-β-farnesense as such or a liquid composition prepared from it. The farnesene need not be entirely pure, but a purity of at least 80% is desirable.

According to the invention the compositions are prepared in a way usual for the preparation of contact insecticides. Solutions or emulsions may be prepared; also aerosol compositions may be prepared. As carriers the known solvents and diluents may be used. From these the following may be mentioned: aromatic hydrocarbons, such as xylene, toluene, chlorinated aromatic or aliphatic hydrocarbons, such as chlorobenzenes, chloroethylenes, dichloromethane, further aliphatic hydrocarbons, such as cyclohexane and petroleum fractions, for example ligroin; alcohols, such as ethanol, propanols, butanols or glycols, ethers, esters and ketones, such as acetone, methylethylketone, methylisobutylketone or cyclohexanone, as well as dimethylformamide and dimethylsulfoxide. Water may be used as a diluent as well. The use of a co-solvent and/or dispersion of the active substance with the aid of a surfactant is necessary when water is used, because the active substance is insoluble or only very sparingly soluble in water. (E)-β-farnesene is fairly soluble in the majority of organic solvents. As examples of emulsifying and/or dispersing agents ionogenic or non-ionogenic emulsifyers, such as alkylsulfonates, arylsulfonates, alkylsulfonates, polyoxyethylene fatty acid esters and polyoxyethylene fatty alcohol ethers may be mentioned.

The concentration of the active substance in the compositions may vary within broad limits. The composition should contain sufficient of the (E)-β-farnesene to kill the aphids by liquid contact. An amount of 0.1–2 μg, applied to an aphid in liquid form appeared to be sufficient to kill the insect. The use of the known ULV-compositions (ULV=ultra low volume) and atomizing apparatus suitable for such compositions is preferred. Compositions having a concentration of at least 10% by weight of the active substance are preferably prepared and used.

The invention is elucidated by means of the following example.

EXAMPLE

Aphids of the species *Myzus persicae* and *Neomyzus circumflexus* in various stages of development were treated with (E)-β-farnesene according to the following methods:

Droplets of 0.01–0.02 μl (10–20 μg) of (E)-β-farnesene were applied to the backs of the aphids by means of a Hamilton syringe of 1.0 μl. The aphids died immediately. Then radish leaves having aphid populations on their surface were sprayed with (E)-β-farnesene by means of a Desaga-sprayer of 5 ml. It was calculated that a concentration of about 0.01–0.02 μl (10–20 μg) of (E)-β-farnesene was present per $mm^2$ of leaf area. Also in this case all of the aphids were killed.

A 10 weight % solution of (E)-β-farnesene in ethanol (96%) was atomized on paprika plants infested with aphids. On each plant 6 $cm^3$ of the solution was used. None of the aphids survived after this treatment.

We claim:

1. A process for killing aphids comprising contacting the aphids with an amount of (E)-β-farnesene effective to kill aphids.

2. A process for killing aphids of the species *Myzus persicae* and *Neomyzus circumflexus* comprising contacting said aphids with an amount of (E)-β-farnesene effective to kill aphids of said species.

3. A process for killing aphids comprising contacting the aphids with a contact insecticide composition in liquid form comprising (E)-β-farnesene and a liquid carrier, the (E)-β-farnesene being present in an amount effective to kill aphids.

4. A process according to claim 3, wherein the liquid carrier is a solvent selected from the group consisting of aromatic hydrocarbons, aliphatic hydrocarbons, alcohols, ketones, dimethylformamide and dimethylsulfoxide.

* * * * *